United States Patent [19]

Barberet et al.

[11] Patent Number: Plant 6,273

[45] Date of Patent: Sep. 6, 1988

[54] CARNATION NAMED 'LONFIDEX'

[75] Inventors: Nicole Barberet; Yves Ducloux, both of Antibes, France

[73] Assignee: Laboratoire de Physiologie Vegetale de la Londe, La Londe, France

[21] Appl. No.: 906,542

[22] Filed: Sep. 12, 1986

[51] Int. Cl.[4] ..... A01H 5/00

[52] U.S. Cl. ..... Plt./70

[58] Field of Search ..... Plt./70

*Primary Examiner*—Robert E. Bagwill

*Attorney, Agent, or Firm*—Charles W. Rummler

[57] ABSTRACT

A new variety of spray carnation having small soft yellow blooms produced profusely at intermittent intervals of spring, midseason and fall, usually appearing in clusters at the upper portion of a strong, erect stem, the flowers being distinguished by the soft yellow color of the petals and the plant itself being distinguished by its moderately height and vigorous, upright and rather rigid habit.

1 Drawing Sheet

BACKGROUND OF THE NEW PLANT

This new carnation variety originated as a seedling resulting from our crossing of plants selected from our collection of carnations maintained for breeding purposes at La Londe, Les Maures, France. Our object in making this crossing being to develop a spray carnation having blooms of good quality and nice color on a strong plant, having resistance to *Fusarium oxysporum.* This plant was reproduced by cuttings with very good results so that further propagation was directed to be carried on through a series of successive generations by means of cuttings from previous plants produced in the same manner. This extended propagation of our new seedlings demonstrated clearly that the novel characteristics of its blooming and growth habits would remain true from generation to generation and appeared to be firmly fixed.

DESCRIPTION OF THE DRAWING

Our new variety of spray carnation is illustrated by the accompanying photographic drawing, which shows in full color the upper portion of a typical spray stem bearing buds and flowers at various stages of growth, the colors shown being as nearly true to those specified as is reasonably possible to obtain by conventional photographic procedures.

DESCRIPTION OF THE NEW PLANT

The following is a detailed description of our new carnation plant based upon observations of greenhouse plants grown at La Londe, Les Maures, France, in the spring of the year, the color designation being according to the R.H.S. Colour Chart published by The Royal Horticultural Society of London, England.

THE PLANT

Origin: Seedling.

Parentage:

*Seed stock.*—Stock Variety 71 MJ 1.

*Pollen plant.*—Stock Variety 76 MB 15. These parent varieties were selected by us from our collection of breeding plants and each is individually identified in our permanent records maintained in our office at La Londe.

Classification:

*Botanic.*—*Dianthius caryophyllus.*

*Commercial.*—Spray carnation.

Form: Bush of moderate spray shape comprising at least four stems emitted from the main stem near the ground.

Main stem:

*Length.*—Less than 15 cm. due to pinching.

Branching character. Branched.

Growth: Vigorous, upright and rigid.

Foliage:

*Quantity.*—Abundant.

*Number of leaves.*—More than 120.

*Size of leaf.*—Averages about 13.1 cm. long and about 1 cm. wide at the seventh node.

*Leaf shape.*—Long with curved margin.

*Texture.*—Leathery.

*Color.*—Both upper and lower sides, 189A.

*Leaflets.*—None.

*Ribs, veins and rachis.*—Hardly noticeable.

THE BUD

Size: Small

*Diameter.*—Averages about 1.6 cm.

*Length.*—Averages about 2.3 cm.

Shape: Ovoid.

Rate of opening: Normal for carnations.

Color or petals:

*When sepals first divide.*—4D.

*When sepals begin to unfurl.*—4C.

Sepals:

*Number.*—About 5.

*Shape.*—Joined together at lower part with the upper part having a sharp, pointed apex. The sepals are hooded over the bud before dividing and continue to stand up as the flower opens.

*Color.*—Inside — 145C. Outside — 144B.

*Striae.*—Longitudinal.

Calyx: Medium and funnel shaped.

*Aspect.*—Smooth.

Flower stem:

*Length.*—About 58.7 cm., in average.

*Character.*—Erect and rather rigid.

*Color.*—189A.

THE FLOWER

Blooming habit: Recurrent, blooming profusely during spring, midseason and fall blooming periods with a tendency to give fewer blooms in the fall.

Size of bloom: Small.
*Diameter.*—Averaging 5.5 cm.
*Depth.*—Averaging 4.5 cm.
Borne: As a cluster.
Shape:
*When bloom first opens.*—High centered.
*When bloom matures.*—Dome shaped.
Petalage:
*Number of petals.*—About 33 in average.
*Arrangement.*—Generally imbricated.
*Petal form.*—Fan shaped with rounded edges and lightly serrated apex.
*Texture.*—Leathery.
*Appearance.*—Satiny.
*Color.*—Both outer and inner petals: Body — 4C., Base — Greenish. Reverse side — 4D.
Petaloids: Less then 4.
*Size.*—Smaller than petals.
*Color.*—Same as petals.
Flower stem:
*Length.*—About 58.7 cm. (cut at tenth node).
*Character.*—Strong and upright.
*Color.*—189A.
Discoloration after full bloom: Weak.
Fragrance: Perceptible.
Persistence: The flowers hang on and dry.
Lasting quality:
*As a cut flower.*—At least ten days in vase keeping.

REPRODUCTIVE ORGANS

Stamens:
*Number.*—9 to 12.
*Arrangement.*—Around the ovary.
*Anthers.*—Size: Less than 4 mm. Color: Yellow.
*Filaments.*—Length: Averages about 1 cm. Color: Yellow.
Pistils:
*Number.*—2 to 3.
*Styles.*—Length: Averaging about 3.6 cm. Color: Yellow.
*Stigmas.*—Color: Yellow.
Ovaries: The ovaries are ribbed.

This new spray carnation variety most nearly resembles the variety 'Londragel' but differs from that variety by having a yellow color, a shorter stem and by being tolerant to *Fusarium oxysporum.*

We claim:

1. The new and distinct variety of spray carnation, substantially as herein shown and described characterized by its intermittent flowering habit with profuse production of flowers having a soft yellow coloration, and having a rigid vigorous and upright growth habit with a normal height of about 84 cm. at eight months with a erect, rigid peduncle averaging about 58.7 cm. in length.

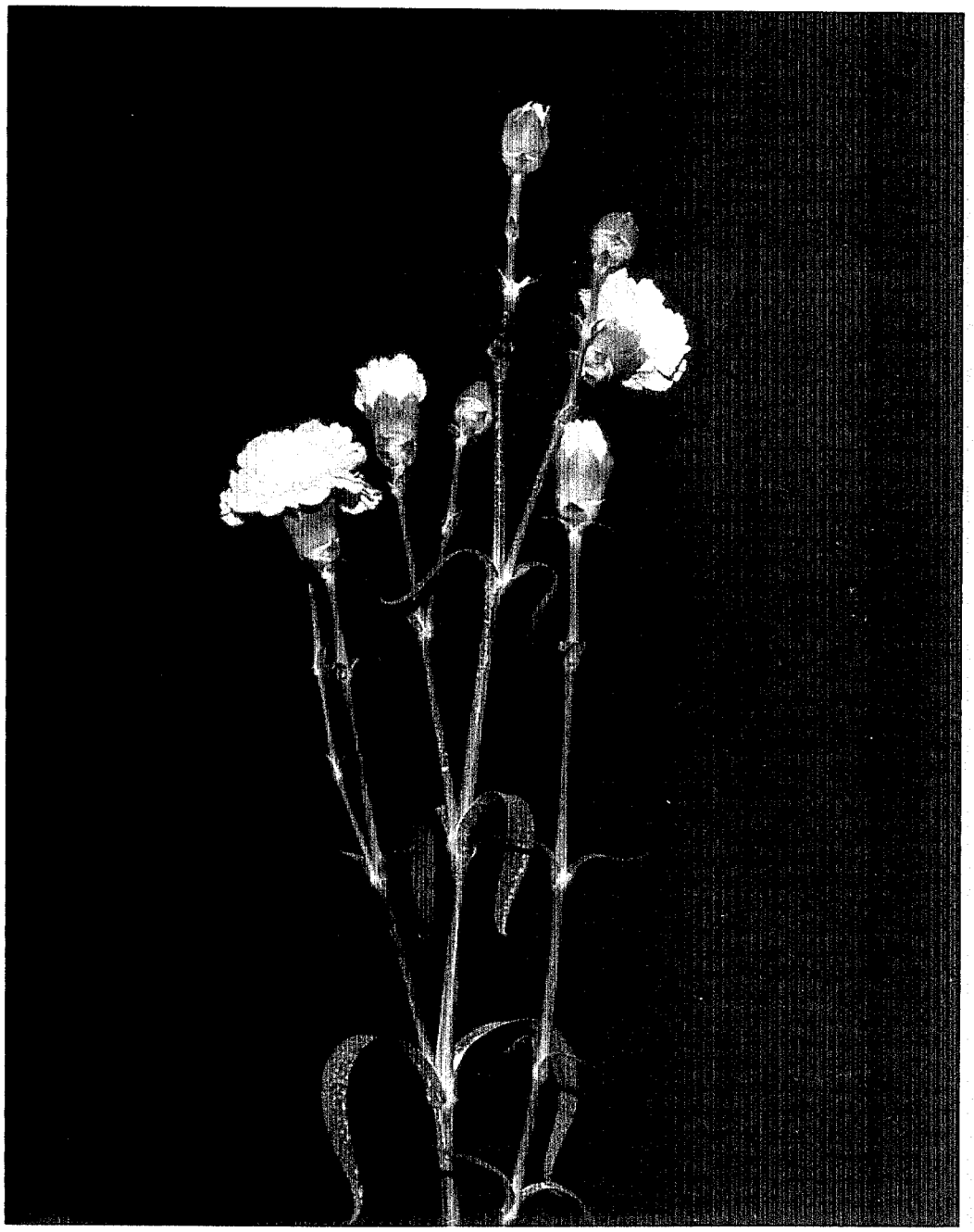

* * * * *